(12) United States Patent
Mou et al.

(10) Patent No.: US 10,881,786 B2
(45) Date of Patent: *Jan. 5, 2021

(54) WEARABLE LIQUID SUPPLYING DEVICE FOR HUMAN INSULIN INJECTION

(71) Applicant: Microjet Technology Co., Ltd., Hsinchu (TW)

(72) Inventors: Hao-Jan Mou, Hsinchu (TW); Li-Pang Mo, Hsinchu (TW); Wei-Ming Lee, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 179 days.

This patent is subject to a terminal disclaimer.

(21) Appl. No.: 16/149,315

(22) Filed: Oct. 2, 2018

(65) Prior Publication Data

US 2019/0125963 A1 May 2, 2019

(30) Foreign Application Priority Data

Oct. 27, 2017 (TW) .............................. 106137205 A

(51) Int. Cl.
*A61M 5/142* (2006.01)
*A61M 37/00* (2006.01)
(Continued)

(52) U.S. Cl.
CPC .... *A61M 5/14248* (2013.01); *A61M 5/14224* (2013.01); *A61M 5/14593* (2013.01);
(Continued)

(58) Field of Classification Search
CPC .... A61M 2005/1726; A61M 2230/201; A61M 5/158; A61M 5/3295; A61M 2005/14252;
(Continued)

(56) References Cited

U.S. PATENT DOCUMENTS 6,132,755 A * 10/2000 Eicher ................ A61M 31/002
424/427
6,558,361 B1 5/2003 Yeshurun
(Continued)

FOREIGN PATENT DOCUMENTS

CN 1190904 A 8/1998
WO WO 2013/070866 A1 5/2003

OTHER PUBLICATIONS

Taiwanese Office Action and Search Report, dated Oct. 4, 2018, for Taiwanese Application No. 106137205.

*Primary Examiner* — Lauren P Farrar
*Assistant Examiner* — Hamza A Darb
(74) *Attorney, Agent, or Firm* — Birch, Stewart, Kolasch & Birch, LLP

(57) ABSTRACT

A wearable liquid supplying device for insulin injection is fixed on a user's body through a ring belt and includes a carrier body, a flow-guiding-and-actuating unit, a sensor, an air bag, a miniature air pump and a driving chip. The sensor measures sweat on human skin to detect a level of the blood glucose. The driving chip receives the glucose monitoring data and accordingly controls the actuation of the flow-guiding-and-actuating unit and the open/closed states of the switching valves. The miniature air pump is enabled to inhale gas into the air bag, so that the air bag is inflated and the ring belt contacts the human skin tightly. The flow-guiding-and-actuating unit is enabled to generate a pressure difference so that the insulin liquid is transported to a liquid guiding outlet through a liquid guiding channel and flows into the microneedle patch for being injected into the subcutaneous tissue.

23 Claims, 12 Drawing Sheets

(51) Int. Cl.
*F04B 45/047* (2006.01)
*A61M 5/158* (2006.01)
*A61M 5/32* (2006.01)
*F04B 43/04* (2006.01)
*F04B 23/02* (2006.01)
*A61M 5/145* (2006.01)
*A61M 5/168* (2006.01)
*A61M 5/172* (2006.01)
*A61B 5/00* (2006.01)

(52) U.S. Cl.
CPC ........ *A61M 5/158* (2013.01); *A61M 5/16813* (2013.01); *A61M 5/3295* (2013.01); *A61M 37/0015* (2013.01); *F04B 23/02* (2013.01); *F04B 43/043* (2013.01); *F04B 45/047* (2013.01); *A61B 5/4266* (2013.01); *A61M 2005/14252* (2013.01); *A61M 2005/1726* (2013.01); *A61M 2037/003* (2013.01); *A61M 2037/0023* (2013.01); *A61M 2205/0244* (2013.01); *A61M 2205/0288* (2013.01); *A61M 2205/0294* (2013.01); *A61M 2205/8206* (2013.01); *A61M 2209/088* (2013.01); *A61M 2210/083* (2013.01); *A61M 2230/201* (2013.01)

(58) Field of Classification Search
CPC .......... A61M 5/14248; A61M 5/14224; A61M 5/14593; A61M 5/16813; A61M 37/0015; A61M 2037/0023; A61M 2210/083; A61M 2205/0244; A61M 2205/0288; A61M 2205/0294; A61M 2205/8206; A61M 2209/088; A61B 5/4266; F04B 45/047; F04B 43/043; F04B 23/02
See application file for complete search history.

(56) References Cited

U.S. PATENT DOCUMENTS

| | | | |
|---|---|---|---|
| 8,646,479 B2 * | 2/2014 | Jaeb | F04B 43/046 137/512.15 |
| 2002/0082543 A1 | 6/2002 | Park et al. | |
| 2014/0188041 A1 * | 7/2014 | Moore | A61B 17/205 604/46 |
| 2015/0057611 A1 * | 2/2015 | Bureau | A61M 37/0015 604/111 |
| 2015/0327871 A1 * | 11/2015 | Fortson | A61B 17/135 606/202 |
| 2017/0095184 A1 * | 4/2017 | Heikenfeld | A61B 5/0531 |
| 2017/0215749 A1 * | 8/2017 | Zhuo | A61B 5/002 |
| 2018/0027931 A1 * | 2/2018 | Baranski | A44C 5/0069 |
| 2019/0085836 A1 * | 3/2019 | Mou | F04B 45/047 |
| 2019/0125964 A1 * | 5/2019 | Mou | F04B 43/046 |

* cited by examiner

WEARABLE LIQUID SUPPLYING DEVICE FOR HUMAN INSULIN INJECTION

FIELD OF THE INVENTION

The present disclosure relates to a liquid supplying device, and more particularly to a wearable liquid supplying device for human insulin injection.

BACKGROUND OF THE INVENTION

Nowadays, the first treatment of type 1 diabetes mellitus and type 2 diabetes mellitus is to supply the patients with hypoglycemic medicines. The way of giving medicines includes oral administration, syringe injection and insulin pump injection. In oral administration and syringe injection, the patients need to take a drop of blood every day for measuring the level of blood glucose by using a blood glucose meter, so that the patients can take medicines according to the measured level of blood glucose. An insulin pump system includes an indwelling needle and an insulin pump. The indwelling needle punctures into the patient's skin and is fixed on the patient's body for collecting blood and medicine injection. The insulin pump is in fluid communication with the indwelling needle and is controlled to release hypoglycemic medicines according to the measured level of blood glucose.

The insulin is not allowed to be provided orally to the patients. In other words, the patients with diabetes mellitus can only take the insulin through injection. However, the syringe and the indwelling needle not only cause the patients pain but also leave a pinhole on the patients' skin. Moreover, since the syringe injection should be given many times a day, it may lead to small lumps in the subcutaneous tissue due to frequent injections. Although the insulin pump has reduced the frequency of injections by using the indwelling needle, however, it is inconvenient to carry the insulin pump in daily life or in exercise due to its certain volume and weight.

Therefore, there is a need of providing a wearable liquid supplying device for human insulin injection to address the above-mentioned issues as using the conventional injection method. The wearable liquid supplying device for human insulin injection is intelligent, safe, portable and painless, allowing the patients to inject insulin in daily life so as to control the level of the blood glucose anytime.

SUMMARY OF THE INVENTION

The object of the present disclosure is to provide a wearable liquid supplying device for human insulin injection to overcome the problems in the current situation, wherein the conventional insulin injection method causes the patients pain and the insulin pump is inconvenient to carry. The wearable liquid supplying device for human insulin injection is intelligent, safe, portable and painless and allows the patients to inject human insulin in daily life so as to control the level of the blood glucose anytime. The wearable liquid supplying device for human insulin injection is served as an artificial pancreas for supplying human insulin automatically.

In accordance with an aspect of the present disclosure, a wearable liquid supplying device for human insulin injection is provided. The wearable liquid supplying device includes a main body, a ring belt, a carrier body, a liquid storage chamber, a flow-guiding-and-actuating unit, plural switching valves, a microneedle patch, a sensor, an air bag, a miniature air pump and a driving chip. The main body has an accommodation space. The ring belt has two ends respectively connected to two opposite sides of the main body. The carrier body is disposed in the accommodation space of the main body. The liquid storage chamber is formed on the carrier body to store insulin liquid and has a liquid storage outlet. The flow-guiding-and-actuating unit is constructed on the carrier body and has a liquid guiding channel in fluid communication with liquid storage outlet of the liquid storage chamber. The liquid guiding channel is further in fluid communication with a liquid guiding outlet, wherein after the flow-guiding-and-actuating unit is actuated, the insulin liquid is transported out from the liquid storage chamber and discharged through the liquid guiding outlet. The switching valves are disposed in the liquid storage outlet and the liquid guiding outlet, respectively. The microneedle patch is attached on a side of the flow-guiding-and-actuating unit to seal the liquid guiding outlet and has plural hollow microneedles adapted to be punctured into the human skin as a minimally invasive procedure, so that the insulin liquid is injected into subcutaneous tissue. The sensor is disposed on the carrier body and adapted to be in contact with the human skin to detect a level of blood glucose by measuring sweat on the human skin. According to the result of detecting blood glucose, the sensor generates glucose monitoring data. The air bag is disposed on an inner side of the ring belt. The miniature air pump is in fluid communication with the air bag. The driving chip is disposed on the carrier body. The driving chip controls the actuation of the flow-guiding-and-actuating unit and the miniature air pump, and also controls an open/closed state of each of the switching valves. Meanwhile, the driving chip receives the glucose monitoring data from the sensor. When the ring belt is worn on the human skin, the driving chip controls the miniature air pump to actuate, so that the air bag is inflated and the ring belt is in close contact with the human skin, by which the plural hollow microneedles of the microneedle patch are punctured into the human skin, wherein when the sensor detects a specific level of blood glucose, the driving chip controls the flow-guiding-and-actuation unit to actuate, and controls the switching valves to be in the open state, by which the insulin liquid within the liquid storage chamber is transported out form the liquid storage chamber, discharged through the liquid guiding outlet and guided into the microneedle patch, such that the insulin liquid is injected into the subcutaneous tissue through the plural hollow microneedles.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
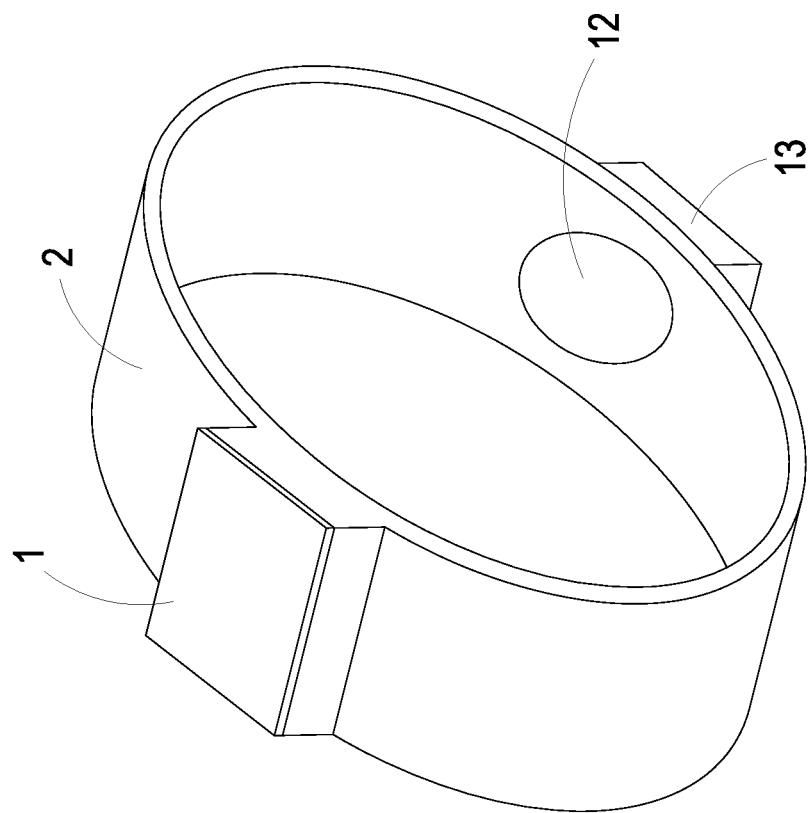
FIG. 1 is a schematic structural view illustrating a wearable liquid supplying device for human insulin injection according to an embodiment of the present disclosure.
Figure 2:
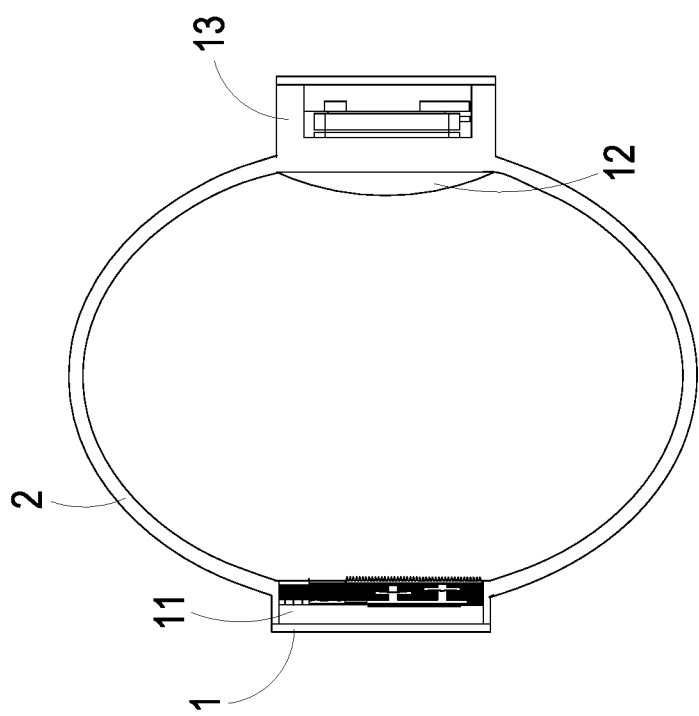
FIG. 2 is a cross sectional view illustrating the wearable liquid supplying device for human insulin injection of FIG. 1.
Figure 3:
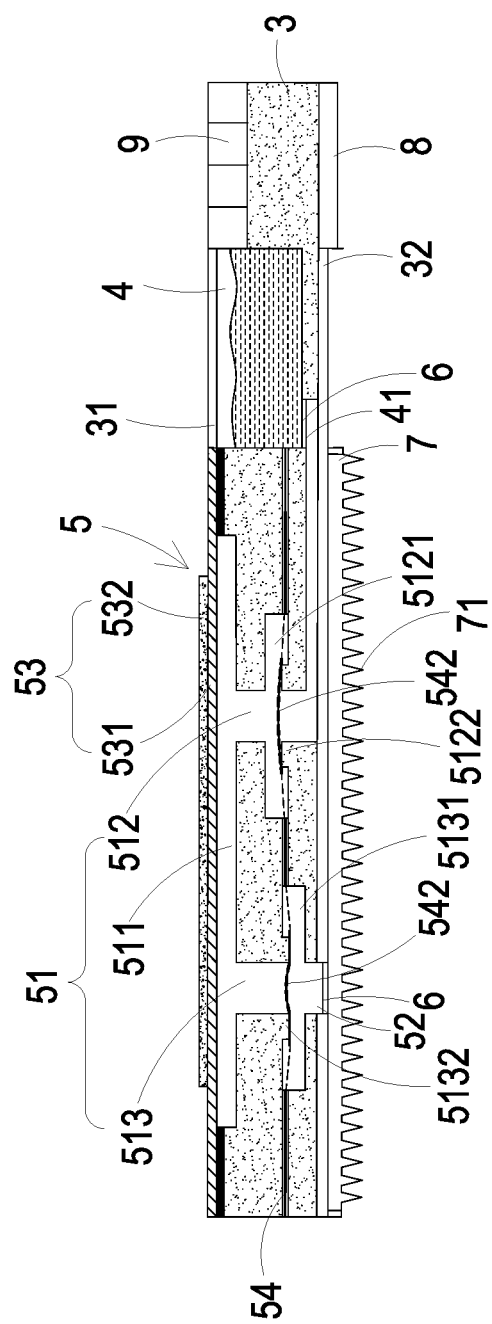
FIG. 3 is a cross sectional view illustrating portions of the wearable liquid supplying device for human insulin injection of FIG. 2.

Please refer to FIGS. 1 to 3. The present discourse provides a wearable liquid supplying device 100 for human insulin injection, wherein the wearable liquid supplying device 100 includes at least one main body 1, at least one accommodation space 11, at least one ring belt 2, at least one carrier body 3, at least one liquid storage chamber 4, at least one liquid storage outlet 41, at least one flow-guiding-and-actuating unit 5, at least one liquid guiding channel 51, at least one liquid guiding outlet 52, at least two switching valves 6, at least one microneedle patch 7, at least one sensor 8, at least one air bag 12, at least one miniature air pump 13 and at least one driving chip 9. The number of the main body 1, the accommodation space 11, the ring belt 2, the carrier body 3, the liquid storage chamber 4, the liquid storage outlet 41, the flow-guiding-and-actuating unit 5, the liquid guiding channel 51, the liquid guiding outlet 52, the microneedle patch 7, the sensor 8, the air bag 12, the miniature air pump 13 and the driving chip 9 is exemplified by one for each in the following embodiments but not limited thereto. It is noted that each of the main body 1, the accommodation space 11, the ring belt 2, the carrier body 3, the liquid storage chamber 4, the liquid storage outlet 41, the flow-guiding-and-actuating unit 5, the liquid guiding channel 51, the liquid guiding outlet 52, the microneedle patch 7, the sensor 8, the air bag 12, the miniature air pump 13 and the driving chip 9 can also be provided in plural numbers.

The present disclosure discloses a wearable liquid supplying device 100 for human insulin injection. Please refer to FIGS. 1, 2 and 3. The wearable liquid supplying device 100 for human insulin injection includes a main body 1, a ring belt 2, a carrier body 3, a liquid storage chamber 4, a flow-guiding-and-actuating unit 5, two switching valves 6, a microneedle patch 7, a sensor 8 and a driving chip 9. The main body 1 has an accommodation space 11. The ring belt 2 has two ends respectively connected to two opposite sides of the main body 1 so that the main body 1 can be fixed on user's body through the ring belt 2 (see FIG. 8). For example, the main body 1 may be fixed on a wrist, an ankle or a neck of the user to be wearable and easy to carry. The carrier body 3 is accommodated within the accommodation space 11 of the maim body 1 and the liquid storage chamber 4 is concavely formed on the carrier body 3 to store the human insulin liquid. The liquid storage chamber 4 has a liquid storage outlet 41 for discharging the insulin liquid within the liquid storage chamber 4. The liquid storage chamber 4 is covered and sealed by a cover plate 31. The flow-guiding-and-actuating unit 5 is constructed on the carrier body 3, comprising a flow guiding channel 51, a liquid guiding outlet 52 and an actuator 53. The flow guiding channel 51 is formed in the carrier body 3, while the liquid guiding outlet 52 is formed on a surface of the carrier body 3 and in fluid communication with the flow guiding channel 51. The flow-guiding channel 51 is further in fluid communication with the liquid storage outlet 41 of the liquid storage chamber 4. After the flow-guiding-and-actuating unit 5 is actuated, a suction force is generated, so that the insulin liquid within the liquid storage chamber 4 is drawn out through the liquid storage outlet 41, flows into the flow guiding channel 51 of the flow-guiding-and-actuating unit 5 and discharged out of the flow-guiding-and-actuating unit 5 through the liquid guiding outlet 52. In this embodiment, the number of the switching valves 6 is two, but not limited thereto. The two switching valves 6 are respectively disposed in the liquid storage outlet 41 and the liquid guiding outlet 52 to seal the liquid storage outlet 41 and the liquid guiding outlet 52. The switching valves 6 are controlled to be in open/closed state so that the amount of the insulin liquid to be transported through the liquid storage outlet 41 and the liquid guiding outlet 52 is controlled, whereby the conditions of supplying excess or insufficient insulin can be prevented. The microneedle patch 7 is attached on a side of the flow-guiding-and-actuating unit 5 and seals the liquid guiding outlet 52. The microneedle patch 7 has plural hollow microneedles 71. After the hollow microneedles 71 have punctured into the patient's skin as a minimally invasive procedure, the insulin liquid is discharged out of the flow-guiding-and-actuating unit 5 through the liquid guiding outlet 52 and injected into the subcutaneous tissue of the patient. The sensor 8 and the driving chip 9 are integrated via microelectronmechanical systems (MEMS) procedure and mounted on the carrier body 3. The sensor 8 is disposed on the carrier body 3 and adapted to contact with the skin of the patient for measuring the sweat on the skin and detecting a level of blood glucose. According to the result of detecting blood glucose, the sensor 8 generates glucose monitoring data. In addition, the main body 1 has a through hole (not shown) adjacent to the skin of the patient. The through hole is in communication with the accommodation space 11 and allows the microneedle patch 7 to contact with the patient's skin therethrough.

The hollow microneedles 71 of the microneedle patch 7 are micron-sized needles capable of puncturing the patient's skin. The hollow microneedles 71 may be made of polymer material, metallic material or silicon material. Preferably but not exclusively, the hollow microneedles 71 are made of silicon dioxide with high biocompatibility. The hollow microneedles 71 have specific diameters for allowing the insulin molecules to pass through. Preferably, the microneedle 71 has an internal diameter ranged from 10 μm to 550 μm. The microneedle 71 has a length ranged from 400 μm to 900 μm. The hollow microneedles 71 can puncture into human's subcutaneous tissue till a depth not in contact with the human's nerve so that the human is painless. The hollow microneedles 71 are disposed on the microneedle patch 7 and arranged in array. Any two adjacent hollow microneedles 71 are spaced from each other at more than 200 μm for avoiding mutual interference. The hollow microneedles 71 arranged in array can prevent the flow injection function from being impacted due to any microneedle 71 is blocked and allow other hollow microneedles 71 to maintain the flow injection function continuously.

Please refer to FIG. 3. The liquid guiding channel 51 of the flow-guiding-and-actuating unit 5 includes a compressing chamber 511, an inlet channel 512 and an outlet channel 513. The inlet channel 512 is in fluid communication with liquid storage outlet 41 of the liquid storage chamber 4. The outlet channel 513 is in fluid communication with the liquid guiding outlet 52. The inlet channel 512 and the outlet channel 513 run through the carrier body 3 and are separated from each other. The compressing chamber 511 is concavely formed on the carrier body 3 and is in fluid communication with a first end of the inlet channel 512 and a first end of the outlet channel 513 as the actuator 53 covers the compressing chamber 511. The inlet channel 512 is formed in the carrier body 3 as a second end of the inlet channel 512 is covered and sealed by a covering component 32, so that a sealed fluid passageway communicating between the second end of the inlet channel 512 and the liquid storage outlet 41 of the liquid storage chamber 4 is constructed. The outlet channel 512 is also formed in the carrier body 3 as a second end of the outlet channel 512 has an outlet aperture on a surface of the carrier body 3 severed as the liquid guiding outlet 52. Consequently, the inlet channel 512, the compressing chamber 511, the outlet channel 513 and the liquid guiding outlet 52 are connected in series and are in fluid communication with each other to form a fluid path.

In some embodiments, the actuator 53 of the flow-guiding-and-actuating unit 5 includes a carrying member 531 and an actuating element 532. The carrying member 531 covers and seals the compressing chamber 511, and the actuating element 532 is attached on a surface of the carrying member 531. The actuating element 532 is subject to a deformation to drive the carrying member 531 to vibrate up and down. Consequently, the volume of the compressing chamber 511 is varied to change the pressure in the interior of the compressing chamber 511 so as to generate a suction force to transport the insulin liquid.

Figure 5:
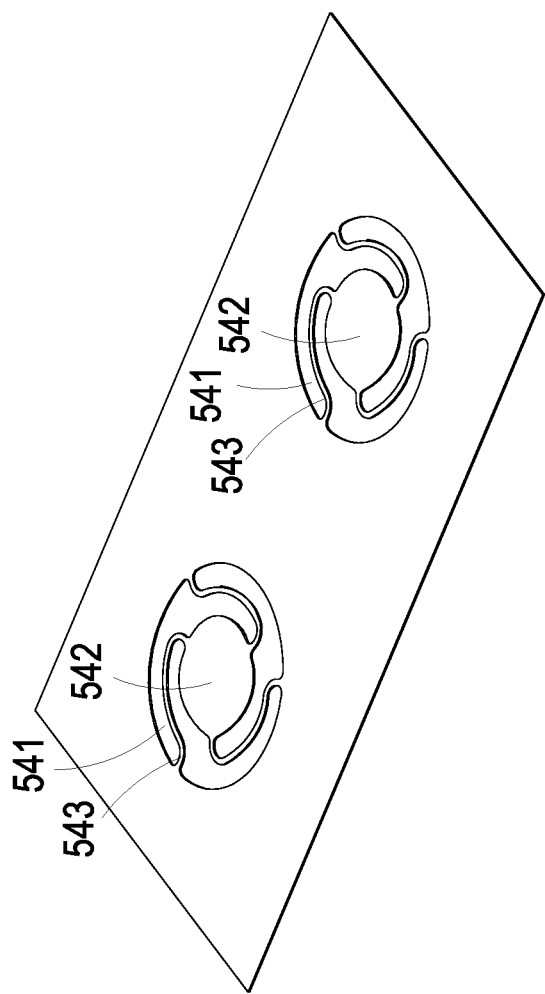
FIG. 5 is a schematic structural view illustrating the valve membrane of the wearable liquid supplying device for human insulin injection according to the present disclosure.

Please refer to FIGS. 3 and 5. A valve membrane 54 is disposed in each of the inlet channel 512 and the outlet channel 513 of the flow-guiding-and-actuating unit 5. At the middle section of the inlet channel 512, there are a chamber 5121 and a convex structure 5122 formed in the carrier body 3, wherein the convex structure 5122 is located in the chamber 5121 close to the second end of the inlet channel 512. Meanwhile, at the middle section of the outlet channel 513, there are a chamber 5131 and a convex structure 5132 formed in the carrier body 3, wherein the convex structure 5132 is located in the chamber 5131 close to the first end of the outlet channel 513. Referring to FIG. 5, the valve membrane 54 has plural through holes 541 spatially corresponding to partial area of the chamber 5121, 5131 and has a central part 542 connected to plural connection parts 543 so that the central part 542 can be elastically supported by the connection parts 543. Consequently, the valve membrane 54 covers and closes the chambers 5121, 5131 located at the inlet channel 512 and the outlet channel 513 so as to drive the central parts 542 to contact and abut against the convex structures 5122, 5132 to form a pre-force.

Figure 4A:
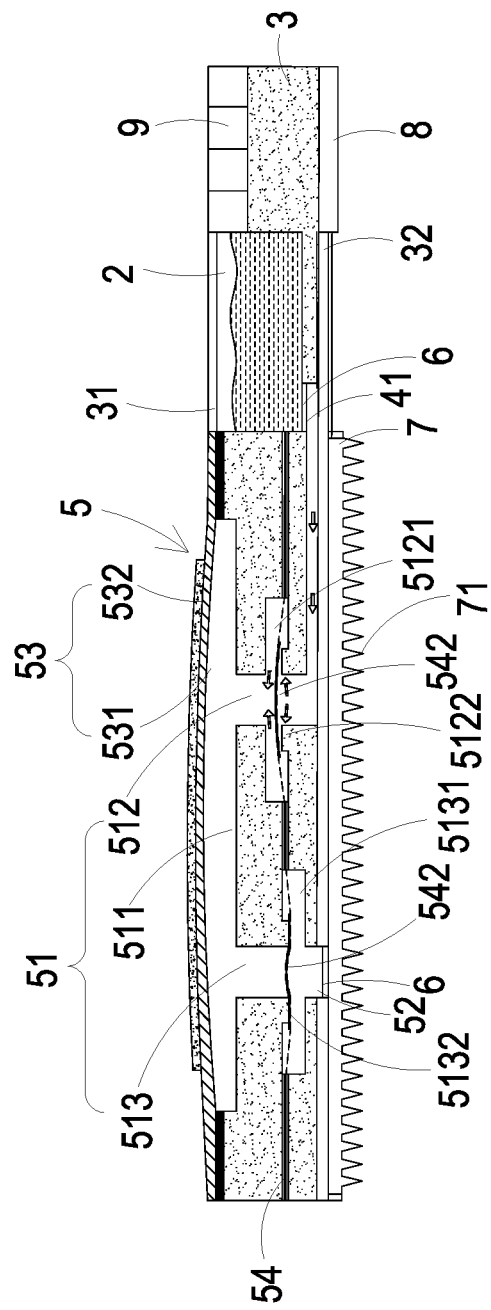
FIGS. 4A and 4B show the actuations of the wearable liquid supplying device for human insulin injection of FIG. 3.
Figure 4B:
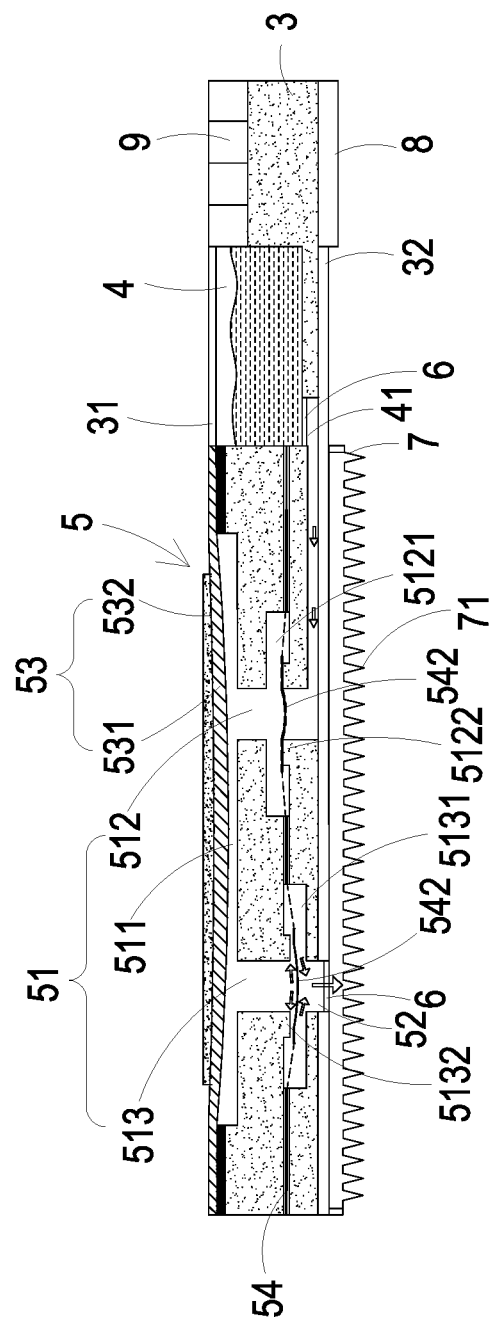

As shown in FIGS. 4A, 4B and 5, when the switching valve 6 in the liquid storage outlet 41 is in an open state as the flow-guiding-and-actuating unit 5 starts to actuate, a pressure difference is generated in the flow-guiding-and-actuating unit 5, driving the central part 542 of the valve membrane 54 in the inlet channel 512 to move upwardly and away from the convex structure 5122. Consequently, the insulin liquid in the inlet channel 512 flows into the compressing chamber 511 through the at least one through hole 541 of the valve membrane 54. Referring to FIG. 4B, after the insulin liquid flows into the compressing chamber 511, in response to the pressure difference within the flow-guiding-and-actuating unit 5, the central part 542 of the valve membrane 54 in the outlet channel 513 moves downwardly and away from the convex structure 5132 in the outlet channel 513 so that the insulin liquid flows toward the liquid guiding outlet 52. In above-mentioned configuration, when the actuator 53 is non-enabled, the central parts 542 of the valve membrane 54 in the inlet channel 512 and the outlet channel 513 can close the inlet channel 512 and the outlet channel 513, respectively. Consequently, the insulin liquid transported between the inlet channel 512 and the outlet channel 513 will not be reversely returned.

Figure 6A:
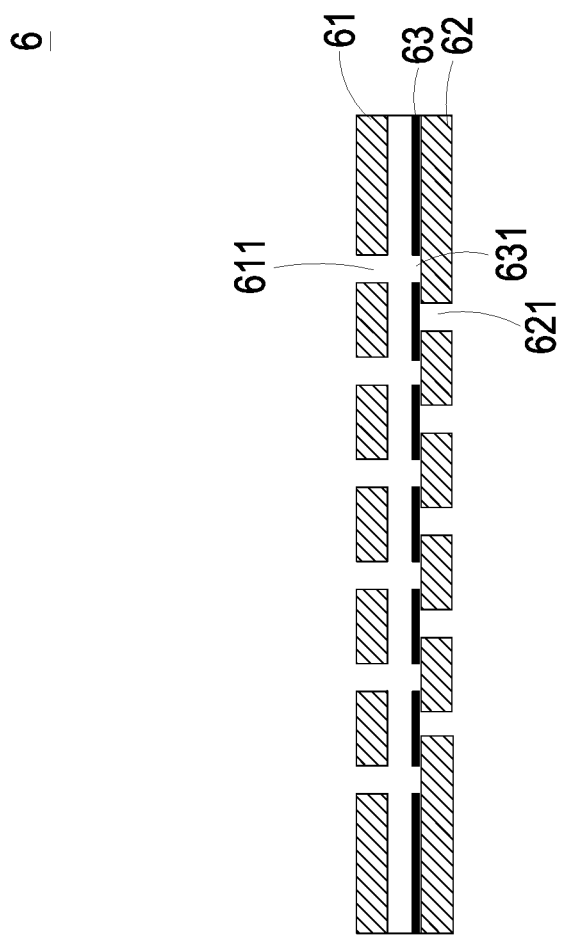
FIG. 6A is a schematic structural view illustrating the switching valve of the wearable liquid supplying device for human insulin injection according to the present disclosure.
Figure 6B:
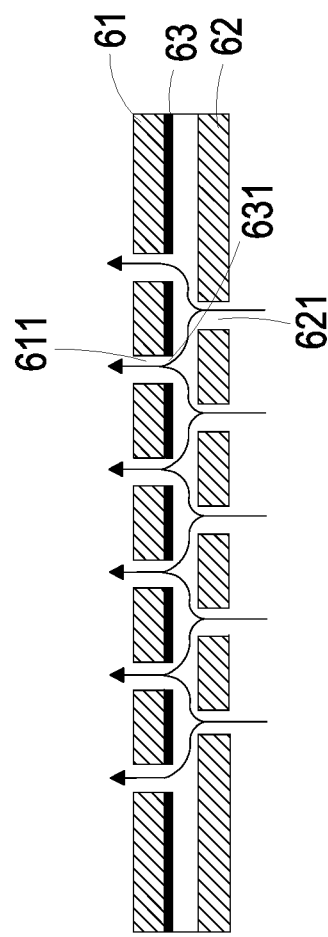
FIG. 6B is schematic diagram illustrating the actuation of switching valve of FIG. 6A.

As shown in FIGS. 6A and 6B, the switching valve 6 includes a stationary component 61, a sealing component 62 and a displacement component 63. The displacement component 63 is disposed and moves between the stationary component 61 and the sealing component 62. The stationary component 61 has at least two orifices 611. The displacement component 63 has at least two orifices 631 respectively corresponding in position to the at least two orifices 611 of the stationary component 61. The sealing component 62 has at least one orifice 621. The at least one orifice 621 of the sealing component 62 is misaligned and staggered with the at least two orifices 611 of the stationary component 61 and the at least two orifices 631 of the displacement component 63. In an embodiment, the stationary component 61, the sealing component 62 and the displacement component 63 are made of a graphene material so as to form a miniature valve element.

In a first aspect of the switching valve 6 in the present disclosure, the displacement component 63 is made of a charged material, and the stationary component 61 is made of a bipolar conductive material. The stationary component 61 is electrically connected to a control circuit of the driving chip 9, so that the electrical polarity (positive polarity or negative polarity) of the stationary component 61 can be controlled by the driving chip 9. In case that the displacement component 63 is made of a negative charged material, while the switching valve 6 is required to be opened, the stationary component 61 is in positive polarity in response to the control of the driving chip 9. Since the displacement component 63 and the stationary component 61 are maintained in reversed polarities, the displacement component 63 moves toward the stationary component 61 to open the switching valve 6 (as shown in FIG. 6B). In contrast, in case that the displacement component 63 is made of the negative charged material, while the switching valve 6 is required to be closed, the stationary component 61 is in negative polarity in response to the control of the driving chip 9. Since the displacement component 63 and the stationary component 61 are maintained in identical polarities, the displacement component 63 moves toward the sealing component 62 to close the switching valve 6 (as shown in FIG. 6A).

In a second aspect of the switching valve 6 in the present disclosure, the displacement component 63 is made of a magnetic material, and the stationary component 61 is made of an electromagnet material and can be controlled to change the electrical polarity. The stationary component 61 is electrically connected to the control circuit of the driving chip 9, so that the electrical polarity (positive polarity or negative polarity) of the stationary component 61 is controlled by the driving chip 9. In case that the displacement component 63 is made of a negative-magnetic material, while the switching valve 6 is required to be opened, the stationary component 61 is in positive polarity in response to the control of the driving chip 9. Since the displacement component 63 and the stationary component 61 are maintained in reversed polarities under control of the driving chip 9, the displacement component 63 moves toward the stationary component 61 to open the switching valve 6 (as shown in FIG. 6B). In contrast, in case that the displacement component 63 is made of a negative-magnetic material, while the switching valve 6 is required to be closed, the stationary component 61 is in negative polarity in response to the control of the driving chip 9. Since the displacement component 63 and the stationary component 61 are maintained in identical polarities, the displacement component 63 moves toward the sealing component 62 to close the switching valve 6 (as shown in FIG. 6A).

Please refer to FIGS. 1 and 2. In this embodiment, the wearable liquid supplying device 100 for human insulin injection further includes an air bag 12 and a miniature air pump 13. The air bag 12 is disposed on an inner surface of the ring belt 2 and towards the user. The miniature air pump 3 is in fluid communication with the air bag 12 and disposed on the ring belt 2. The miniature air pump 13 is electrically connected to the driving chip 9. The miniature air pump 13 is enabled after receiving an inflating signal issued from the driving chip 9. The miniature air pump 13 inhales gas from the surroundings and transports the gas to the air bag 12 to inflate the air bag 12. As the air bag 12 is inflated to be expanded, the ring belt 2 is in close contact with the human skin, and the hollow microneedles 71 of the microneedle patch 7 puncture into the human skin for insulin liquid injection.

Figure 7:
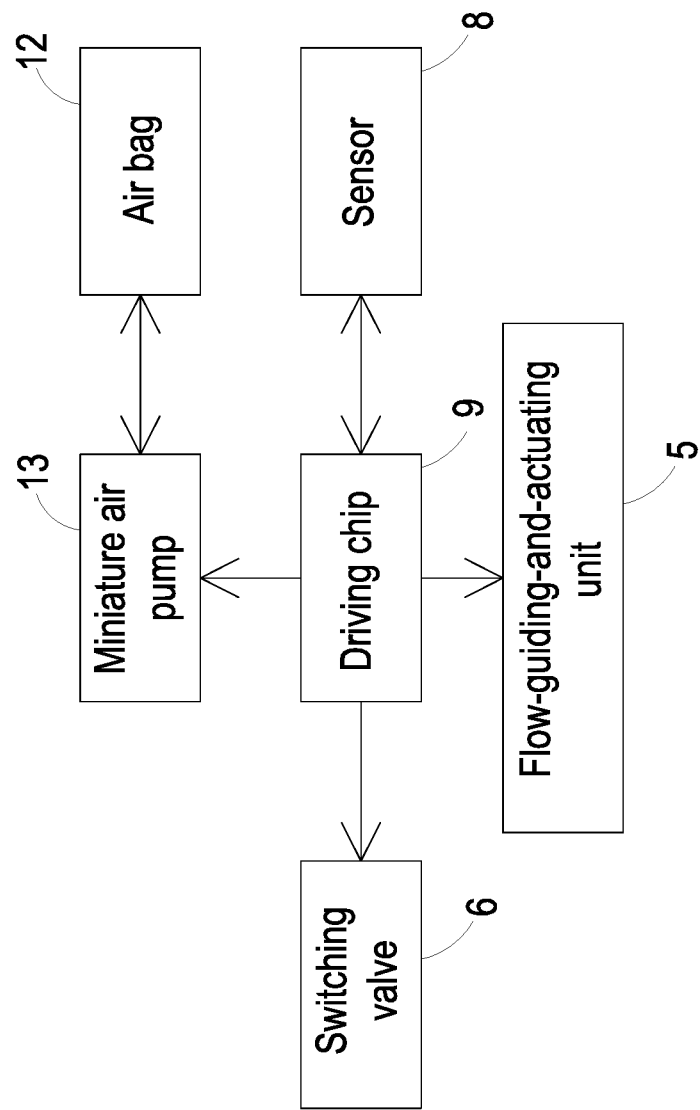
FIG. 7 is a block diagram of the wearable liquid supplying device for human insulin injection according to the embodiment of the present disclosure.

Please refer to FIG. 7, which is a block diagram of the wearable liquid supplying device for human insulin injection according to the embodiment of the present disclosure. The electrical connections among the components of the wearable liquid supplying device 100 are shown in FIG. 7. The driving chip 9 disposed on the carrier body 3 is electrically connected to the miniature air pump 3, the flow-guiding-and-actuating unit 5, plural switching valves 6 and the sensor 8. The sensor 8 is adapted to be in contact with the human skin to monitor the level of blood glucose and accordingly generating glucose monitoring data. After the driving chip 9 receives the glucose monitoring data from the sensor 8, the driving chip 9 determines whether to perform the insulin liquid injection by enabling the flow-guiding-and-actuating unit 5 and controlling the switching valves 6 to be in the open state. Preferably but not exclusively, the driving chip 9 includes a graphene battery (not shown) to supply power.

Figure 8:
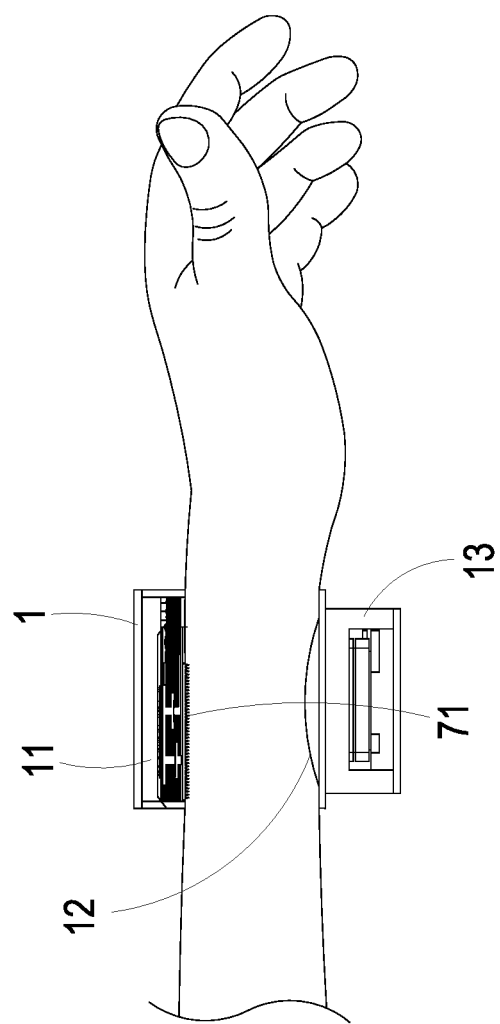
FIG. 8 is a schematic structural view illustrating the wearable liquid supplying device for human insulin injection to be worn on user's body.

Please refer to FIG. 8, which is a schematic structural view illustrating the wearable liquid supplying device for human insulin injection to be worn on user's body. While the miniature air pump 13 is enabled in response to the inflating signal issued from the driving chip 9, the miniature air pump 13 inhales gas from the surroundings and transports the gas to the air bag 12 to inflate the air bag 12. As a result, the hollow microneedles 71 of the microneedle patch 7 puncture into the human skin for performing the insulin liquid injection.

Figure 9A:
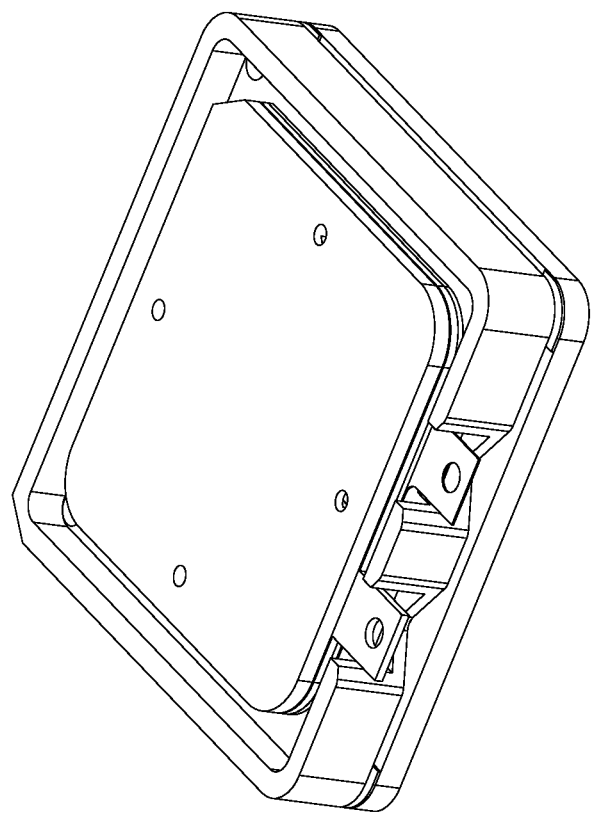
FIG. 9A is a schematic structural view illustrating the miniature air pump of the wearable liquid supplying device for human insulin injection according to the present disclosure.
Figure 9B:
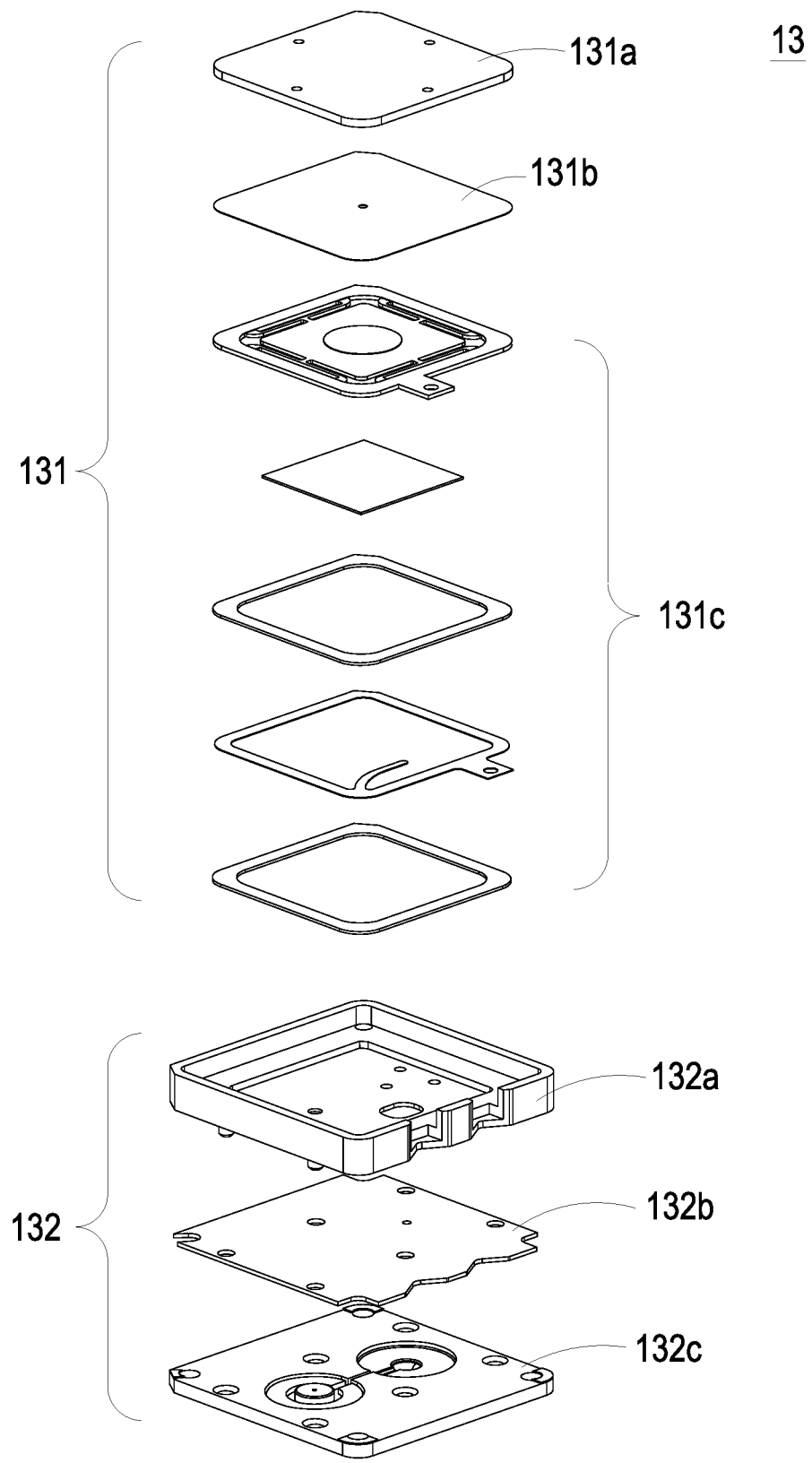
FIG. 9B is a schematic exploded view illustrating the miniature air pump of FIG. 9A.

Please refer to FIGS. 9A and 9B. In this embodiment, the miniature air pump 13 may be a piezoelectric actuating miniature pneumatic device. The miniature pneumatic device includes a miniature air transportation device 131 and a miniature valve device 132. While the gas is transported from the miniature air transportation device 131 to the interior of the miniature valve device 132, a gas-collection action or a gas-releasing action is performed. The miniature air transportation device 131 includes a gas inlet plate 131a, a resonance plate 131b and a piezoelectric actuator 131c, which are stacked on each other sequentially. While the piezoelectric actuator 131c is enabled, the gas is inhaled into the miniature air transportation device 131 through the gas inlet plate 131a and transported downwardly to the miniature valve device 132 for allowing the gas to flow in single direction. The miniature valve device 132 includes a gas collecting plate 132a, a valve piece 132b and a gas outlet plate 132c, which are stacked on each other sequentially. The outlet plate 132c has an outlet end (not shown) in fluid communication with the air bag 12. While the gas is transported from the miniature air transportation device 131 to the interior of the miniature valve device 132, the gas is transported to the air bag 12 through the outlet end of the gas outlet plate 132 for performing the gas-collection action or the gas is discharged out through a pressure-releasing aperture of the gas outlet plate 132c for performing the gas-releasing action.

In summary, the present disclosure provides a wearable liquid supplying device for human insulin injection. The flow-guiding-and-actuating unit is enabled to generate a pressure gradient to transport the insulin liquid out from the liquid storage chamber. Then, the insulin liquid is injected into the user's skin through the microneedle patch so as to supply the insulin for the user. The sensor measures the level of blood glucose of the user, and the driving chip controls the actuation of the flow-guiding-and-actuating unit and the open/closed states of the switching valves so as to adjust the amount and flow rate of the insulin liquid to be injected into the user. In addition, the wearable liquid supplying device uses an air bag to reduce the distance between the user skin and the microneedles such that the microneedle patch can puncture into the skin of the user properly. Moreover, the miniature air pump is used to adjust the gas amount within the air bag so as to finely adjust the depth which the microneedle patch punctures into the skin of the user. Thus, the wearable liquid supplying device for human insulin injection of the present disclosure can provide the functions of pancreas and be served as a substitution of a conventional artificial pancreas.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A wearable liquid supplying device for human insulin injection, comprising:
    a main body having an accommodation space;
    a ring belt having two ends respectively connected to two opposite sides of the main body;
    a carrier body disposed in the accommodation space of the main body;

a liquid storage chamber formed in the carrier body to store insulin liquid and having a liquid storage outlet;

a flow-guiding-and-actuating unit constructed on the carrier body and having a liquid guiding channel in fluid communication with the liquid storage outlet of the liquid storage chamber, the liquid guiding channel being further in fluid communication with a liquid guiding outlet, wherein after the flow-guiding-and-actuating unit is actuated, the insulin liquid is transported out from the liquid storage chamber and discharged through the liquid guiding outlet;

at least two switching valves disposed in the liquid storage outlet and the liquid guiding outlet, respectively;

a microneedle patch attached on a side of the flow-guiding-and-actuating unit to seal the liquid guiding outlet, the microneedle patch having plural hollow microneedles adapted to be punctured into a human skin as a minimally invasive procedure such that the insulin liquid is injected into subcutaneous tissue;

a sensor disposed on the carrier body and adapted to be in contact with the human skin to detect a level of the blood glucose by measuring sweat on the human skin, after which the sensor accordingly generates glucose monitoring data;

an air bag disposed on an inner side of the ring belt;

a miniature air pump in fluid communication with the air bag; and a driving chip disposed on the carrier body, controlling the actuation of the flow-guiding-and-actuating unit and the miniature air pump, and controlling an open/closed state of each of the at least two switching valves, the driving chip receiving the glucose monitoring data from the sensor;

wherein when the ring belt is worn on the human skin, the driving chip controls the miniature air pump to actuate, so that the air bag is inflated and the ring belt is in close contact with the human skin, by which the plural hollow microneedles of the microneedle patch are punctured into the human skin, wherein when the sensor detects a specific level of blood glucose, the driving chip controls the flow-guiding-and-actuation unit to actuate, and controls the at least two switching valves to be in the open state, by which the insulin liquid within the liquid storage chamber is transported out form the liquid storage chamber, discharged through the liquid guiding outlet and guided into the microneedle patch, such that the insulin liquid is injected into the subcutaneous tissue through the plural hollow microneedles.

2. The wearable liquid supplying device for human insulin injection according to claim 1, wherein the flow guiding channel of the flow-guiding-and-actuation unit includes a compressing chamber, an inlet channel and an outlet channel, the inlet channel is in fluid communication with the liquid storage outlet of the liquid storage chamber, the outlet channel is in fluid communication with the liquid guiding outlet, and the inlet channel and the outlet channel are separated from each other and are in fluid communication with each other through the compressing chamber, wherein the flow-guiding-and-actuating unit includes an actuator covering and sealing the compressing chamber, and the actuator is driven to compress the volume of the compressing chamber so that the insulin liquid is compressed to flow.

3. The wearable liquid supplying device for human insulin injection according to claim 2, wherein the flow-guiding-and-actuating unit comprises a carrying member and an actuating element, the carrying member covers and seals the compressing chamber, and the actuating element is attached to a surface of the carrying member, wherein the actuating element is subject to deformation to drive the carrying member to vibrate up and down so as to compress the volume of the compressing chamber and the insulin liquid is compressed to flow.

4. The wearable liquid supplying device for human insulin injection according to claim 3, wherein the actuating element is a piezoelectric component.

5. The wearable liquid supplying device for human insulin injection according to claim 2, wherein a valve membrane is disposed in each of the inlet channel and the outlet channel to control the open/closed state of the inlet channel and the outlet channel in response to the actuation of the flow-guiding-and-actuating unit which compresses the volume of the compressing chamber.

6. The wearable liquid supplying device for human insulin injection according to claim 5, wherein the carrier body further comprises a convex structure in each of the inlet channel and the outlet channel to provide a pre-force when the valve membrane is abutting against the convex structure such that the insulin back flow is prevented.

7. The wearable liquid supplying device for human insulin injection according to claim 1, wherein the driving chip comprises a graphene battery for providing power.

8. The wearable liquid supplying device for human insulin injection according to claim 1, wherein each of the at least two switching valves comprises a stationary component, a sealing component and a displacement component, wherein the displacement component is disposed between the stationary component and the sealing component, and each of the stationary component, the sealing component and the displacement component has plural orifices, wherein the plural orifices of the stationary component are corresponding in position to the plural orifices of the displacement component, and the plural orifices of the sealing component are misaligned and staggered with the plural orifices of the stationary component.

9. The wearable liquid supplying device for human insulin injection according to claim 8, wherein the displacement component is made of a charged material, and the stationary component is made of a bipolar conductive material, wherein the displacement component and the stationary component are maintained in reversed polarities, the displacement component moves close to the stationary component so as to open each of the at least two switching valves.

10. The wearable liquid supplying device for human insulin injection according to claim 9, wherein the polarity of the stationary component is controlled by the driving chip.

11. The wearable liquid supplying device for human insulin injection according to claim 8, wherein the displacement component is made of a charged material, and the stationary component is made of a bipolar conductive material, wherein the displacement component and the stationary component are maintained in identical polarities, the displacement component moves close to the sealing component so as to close each of the at least two switching valves.

12. The wearable liquid supplying device for human insulin injection according to claim 11, wherein the polarity of the stationary component is controlled by the driving chip.

13. The wearable liquid supplying device for human insulin injection according to claim 8, wherein the displacement component is made of a magnetic material, and the stationary component is made of an electromagnet material, wherein the displacement component and the stationary component are maintained in reversed polarities, the displacement component moves close to the stationary component so as to open each of the at least two switching valves.

14. The wearable liquid supplying device for human insulin injection according to claim 13, wherein the polarity of the stationary component is controlled by the driving chip.

15. The wearable liquid supplying device for human insulin injection according to claim 8, wherein the displacement component is made of a magnetic material, and the stationary component is made of an electromagnet material, wherein the displacement component and the stationary component are maintained in identical polarities, the displacement component moves close to the sealing component so as to close each of the at least two switching valves.

16. The wearable liquid supplying device for human insulin injection according to claim 15, wherein the polarity of the stationary component is controlled by the driving chip.

17. The wearable liquid supplying device for human insulin injection according to claim 1, wherein the miniature air pump is a piezoelectric actuating miniature pneumatic device, and the miniature pneumatic device comprises a miniature air transportation device and a miniature valve device, wherein while the gas is transported from the miniature air transportation device to an interior of the miniature valve device, a gas-collection action or a gas-releasing action is performed.

18. The wearable liquid supplying device for human insulin injection according to claim 17, wherein the miniature air transportation device comprises a gas inlet plate, a resonance plate and a piezoelectric actuator, which are stacked sequentially, wherein while the piezoelectric actuator is enabled, the gas is inhaled into the miniature air transportation device through the gas inlet plate and transported downwardly to the miniature valve device for allowing the gas to flow in single direction, wherein the miniature valve device includes a gas collecting plate, a valve piece and a gas outlet plate, which are stacked sequentially, wherein the gas outlet plate has an outlet end in fluid communication with the air bag, wherein while the gas is transported from the miniature air transportation device to the interior of the miniature valve device, the gas is transported to the air bag through the outlet end of the gas outlet plate for performing the gas-collection action or the gas is discharged out through a pressure-releasing aperture of the gas outlet plate for performing the gas-releasing action.

19. The wearable liquid supplying device for human insulin injection according to claim 1, wherein each of the plural hollow microneedles of the microneedle patch has an internal diameter ranged from 10 μm to 550 μm.

20. The wearable liquid supplying device for human insulin injection according to claim 1, wherein each of the plural hollow microneedles of the microneedle patch has a length ranged from 400 μm to 900 μm.

21. The wearable liquid supplying device for human insulin injection according to claim 1, wherein the plural hollow microneedles are arranged in array, and any two adjacent ones of the plural hollow microneedles are spaced from each other at more than 200 μm.

22. The wearable liquid supplying device for human insulin injection according to claim 1, wherein the plural hollow microneedles are made of silicon dioxide.

23. A wearable liquid supplying device for human insulin injection, comprising:
   at least one main body having at least one accommodation space;
   at least one ring belt having two ends respectively connected to two opposite sides of each of the at least one main body;
   at least one carrier body disposed in one of the at least one accommodation space of one of the at least one main body;
   at least one liquid storage chamber formed in each of the at least one carrier body to store insulin liquid and having at least one liquid storage outlet;
   at least one flow-guiding-and-actuating unit constructed on each of the at least one carrier body and having at least one liquid guiding channel in fluid communication with each of the at least one liquid storage outlet of each of the at least one liquid storage chamber, each of the at least one liquid guiding channel being further in fluid communication with each of the at least one liquid guiding outlet, wherein after each of the at least one flow-guiding-and-actuating unit is actuated, the insulin liquid is transported out from each of the at least one liquid storage chamber and discharged through each of the at least one liquid guiding outlet;
   at least two switching valves disposed in each of the at least one liquid storage outlet and each of the at least one liquid guiding outlet, respectively;
   at least one microneedle patch attached on a side of each of the at least one flow-guiding-and-actuating unit to seal each of the at least one liquid guiding outlet, each of the at least one microneedle patch having plural hollow microneedles adapted to be punctured into a human skin as a minimally invasive procedure such that the insulin liquid is injected into subcutaneous tissue;
   at least one sensor disposed on each of the at least one carrier body and adapted to be in contact with the human skin to detect a level of the blood glucose by measuring sweat on the human skin, after which the sensor accordingly generates glucose monitoring data;
   at least one air bag disposed on an inner side of each of the at least one ring belt;
   at least one miniature air pump in fluid communication with each of the at least one air bag; and
   at least one driving chip disposed on each of the at least one carrier body, controlling the actuation of each of the at least one flow-guiding-and-actuating unit and each of the at least one miniature air pump, and controlling an open/closed state of each of the at least two switching valves, each of the at least one driving chip receiving the glucose monitoring data from each of the at least one sensor;
   wherein when each of the at least one ring belt is worn on the human skin, each of the at least one driving chip controls each of the at least one miniature air pump to actuate, so that each of the at least one air bag is inflated and each of the at least one ring belt is in close contact with the human skin, by which the plural hollow microneedles of each of the at least one microneedle patch are punctured into the human skin, wherein when each of the at least one sensor detects a specific level of blood glucose, each of the at least one driving chip controls each of the at least one flow-guiding-and-actuation unit to actuate, and controls each of the at least two switching valves to be in the open state, by which the insulin liquid within each of the at least one liquid storage chamber is transported out from each of the at least one liquid storage chamber, discharged through each of the at least one liquid guiding outlet and guided into each of the at least one microneedle patch, such that the insulin liquid is injected into the subcutaneous tissue through the plural hollow microneedles.

* * * * *